(12) United States Patent
Jun et al.

(10) Patent No.: US 11,884,852 B2
(45) Date of Patent: Jan. 30, 2024

(54) HIGHLY SENSITIVE METHODS FOR DETECTING BIOMOLECULES BASED ON MULTIPLE QUANTUM DOTS

(71) Applicants: BIOSQUARE INC., Seongnam-si (KR); KONKUK UNIVERSITY INDUSTRIAL COOPERATION CORP, Seoul (KR)

(72) Inventors: Bong Hyun Jun, Seoul (KR); Sung Wook Yoon, Anyang-si (KR); Yoon Sik Lee, Anyang-si (KR); Dong Ok Choi, Yongin-si (KR); Xuan Hung Pham, Seoul (KR); Tae Han Kim, Goyang-si (KR); Jung Won Kim, Hwaseong-si (KR)

(73) Assignees: BIOSQUARE INC., Seongnam-si (KR); KONKUK UNIVERSITY INDUSTRIAL COOPERATION CORP, Seoul (KR)

( * ) Notice: Subject to any disclaimer, the term of this patent is extended or adjusted under 35 U.S.C. 154(b) by 565 days.

(21) Appl. No.: 16/650,794

(22) PCT Filed: Sep. 28, 2018

(86) PCT No.: PCT/KR2018/011553
§ 371 (c)(1),
(2) Date: Mar. 25, 2020

(87) PCT Pub. No.: WO2019/066567
PCT Pub. Date: Apr. 4, 2019

(65) Prior Publication Data
US 2021/0380876 A1    Dec. 9, 2021

(30) Foreign Application Priority Data

Sep. 28, 2017  (KR) .................. 10-2017-0126515

(51) Int. Cl.
*C09K 11/02* (2006.01)
*C09K 11/88* (2006.01)
*G01N 33/58* (2006.01)

(52) U.S. Cl.
CPC .......... *C09K 11/025* (2013.01); *C09K 11/883* (2013.01); *G01N 33/588* (2013.01)

(58) Field of Classification Search
CPC . C09K 11/646; C09K 11/0883; H01L 33/507; H01L 33/502
See application file for complete search history.

(56) References Cited

U.S. PATENT DOCUMENTS 6,479,146 B1 * 11/2002 Caruso ..................... B01J 13/22
428/407
2003/0082237 A1 * 5/2003 Cha ......................... B82Y 5/00
424/490

(Continued)

FOREIGN PATENT DOCUMENTS

KR   1020090044293 A   5/2009
KR    101165100 B1    7/2012

(Continued)

OTHER PUBLICATIONS

The extended European search report of 18 860 997.8, dated Mar. 15, 2021.

(Continued)

*Primary Examiner* — Brian Turner
(74) *Attorney, Agent, or Firm* — STIP Law Group, LLC

(57) ABSTRACT

The present invention is to provide multilayered multiple quantum dot-doped nanoparticles, each of the multiple quantum dot-doped nanoparticles has a structure consisting of an inorganic core particle, a quantum dot-embedded layer, and a silica/quantum dot composite shell. The multiple quantum dot-doped nanoparticles can be used to detect biomolecules with improved quantum yield (QY) and (Continued)

brightness while maintaining a large area covered by the quantum dots and stable bonds of the quantum dots. Therefore, the multiple quantum dot-doped nanoparticles are suitable for bioapplications, including bioplatforms and highly sensitive methods for detecting biomolecules.

7 Claims, 12 Drawing Sheets

(56) References Cited

U.S. PATENT DOCUMENTS

| | | | |
|---|---|---|---|
| 2006/0019098 A1* | 1/2006 | Chan | C09K 11/883 427/212 |
| 2010/0224831 A1 | 9/2010 | Woo et al. | |
| 2014/0302527 A1 | 10/2014 | Lee et al. | |
| 2016/0041172 A1 | 2/2016 | Lee et al. | |
| 2017/0121603 A1 | 5/2017 | Gu et al. | |
| 2017/0368535 A1* | 12/2017 | Chopra | C01B 32/194 |
| 2018/0126497 A1* | 5/2018 | Campbell | B23K 1/0016 |

FOREIGN PATENT DOCUMENTS

| | | |
|---|---|---|
| KR | 1020150121722 A | 10/2015 |
| WO | WO2014030985 A1 | 2/2014 |

OTHER PUBLICATIONS

Daniel. Gomez et al., Tunable Whispering Gallery Mode Emission from Quantum-Dot-Doped Microspheres, small, 2005, No. 2, pp. 238-241, Wiley-VCH Verlag Gmbh & Co. KGaA, Weinheim, Germany.

Veronica Salgueirino-Maceira et al., Composite Silica Spheres with Magnetic and Luminescent Functionalities, Advanced Functional Materials, 2006, No. 16, pp. 509-514, Wiley-VCH Verlag Gmbh& Co. KGaA, Weinheim, Germany.

Yicheng Wu et al, A Novel Magneto-fluorescent Nano-bioprobe for Cancer Cell Targeting, Imaging and Collection, Applied Biochemistry and Biotechnology, Oct. 16, 2010, vol. 163, No. 7, pp. 813-825, Springer, New York, USA.

International Search Report of PCT/KR2018/011553, dated Jan. 11, 2019, English translation.

Ivan Castello Serrano et al., QD-"Onion"-Multicode silica nanospheres with remarkable stability as pH sensors, Journal of Materials Chemistry, 2011, pp. 17673-17679, vol. 21, The Royal Society of Chemistry, London, United Kingdom.

Kwan Hyi Lee et al, Nanosensor technology for sensitive detection of high risk pathogens, Academic Research and Service Project Final Report, 2013, pp. 1-49, Korea Centers for Disease Control and Prevention, Cheongju-si, South Korea, English translation of summary.

Shijia Wu et al. Simultaneous detection of enterovirus 71 and coxsackievirus A16 using dual-colour upconversion luminescent nanoparticles as labels, ChemComm, 2012, pp. 4866-4868, vol. 48, The Royal Society of Comistry, London, United Kingdom.

Chole Kim and Peter C. Searson, Magnetic bead-quantum dot assay for detection of a biomarker for traumatic brain injury, Nanoscale, 2015, pp. 17820-17826, vol. 7, The Royal Society of Comistry, London, United Kingdom.

\* cited by examiner

[Fig. 1A]
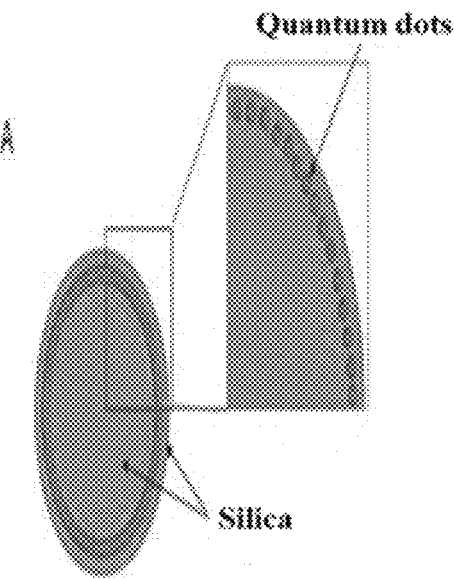
Multiple quantum dots
[Fig. 1B]
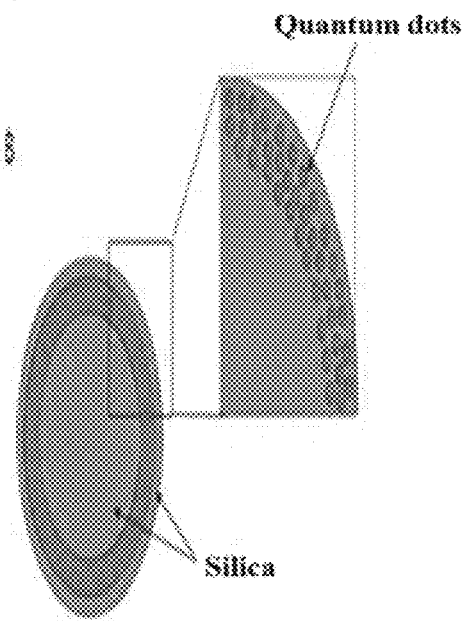
Multilayered multiple quantum dots

[Fig. 2A]
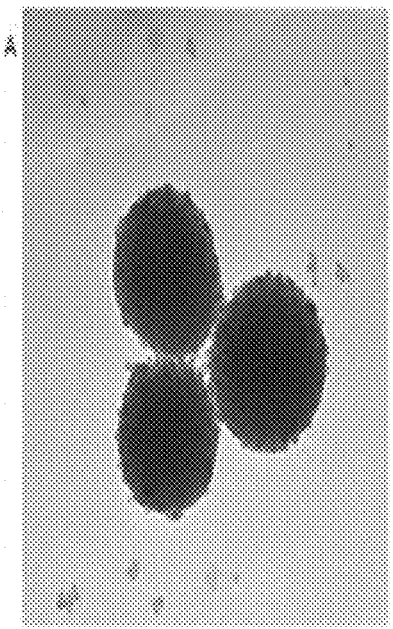
Multiple quantum dots
[Fig. 2B]
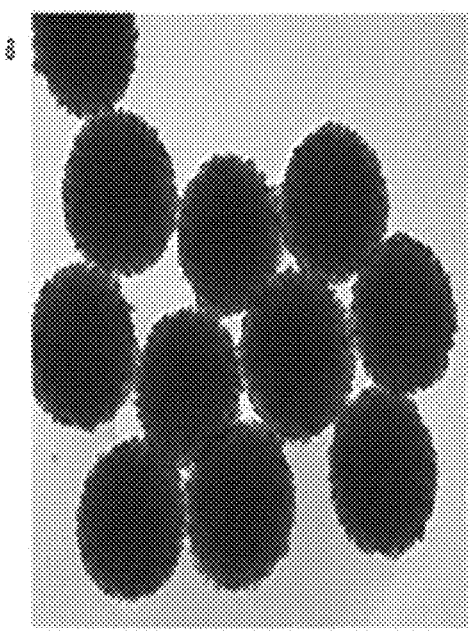
Multilayered multiple quantum dots

[Fig. 3A]
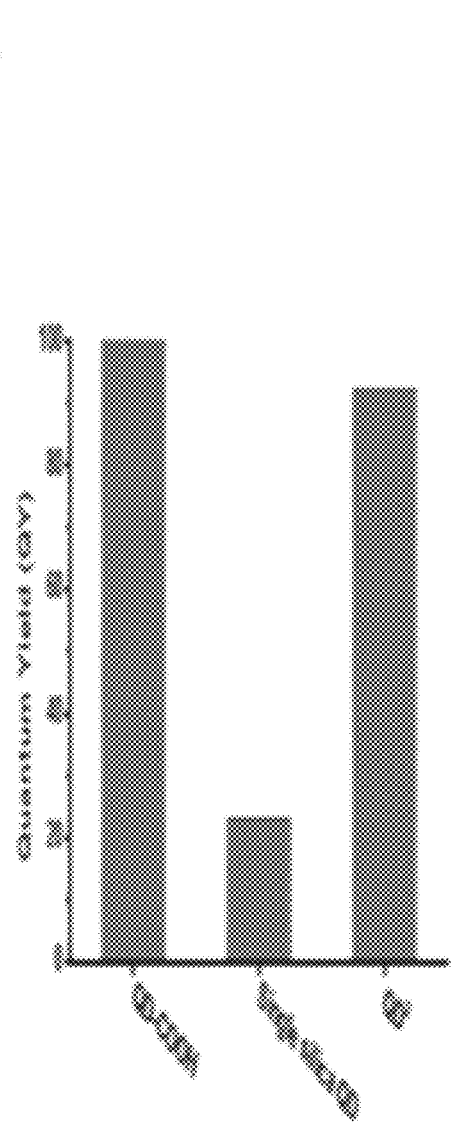

[Fig. 3B]
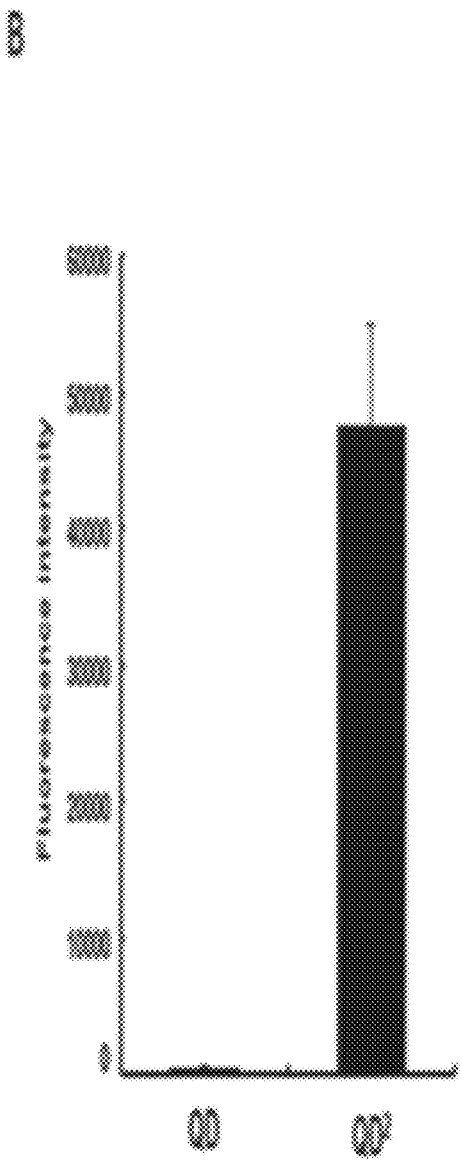

[Fig. 3C]
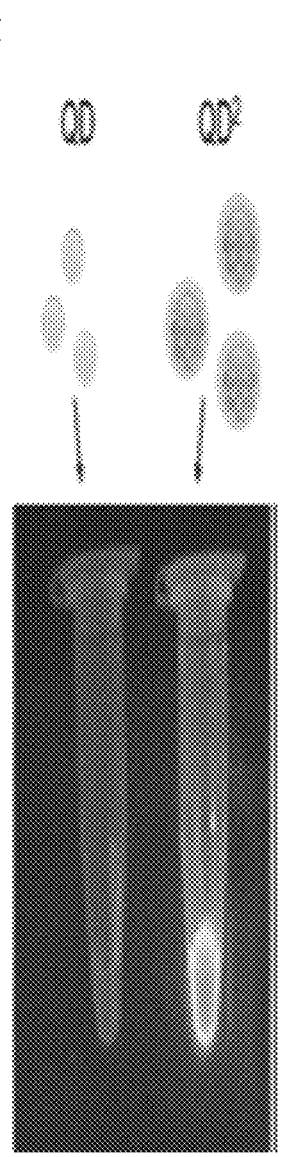

[Fig. 4A]
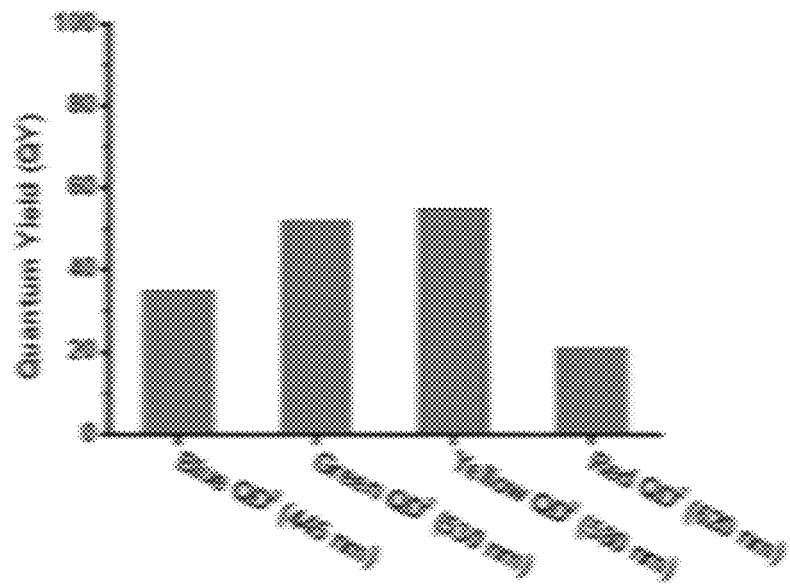
[Fig. 4B]
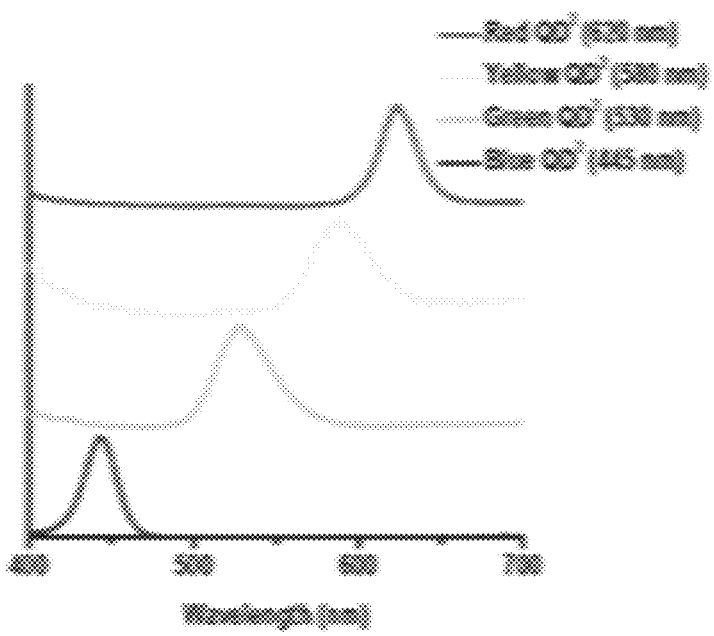

[Fig. 4C]
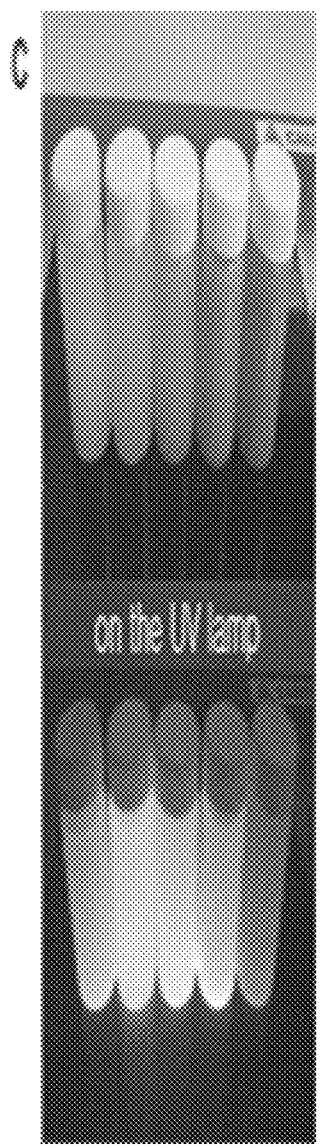

[Fig. 5]
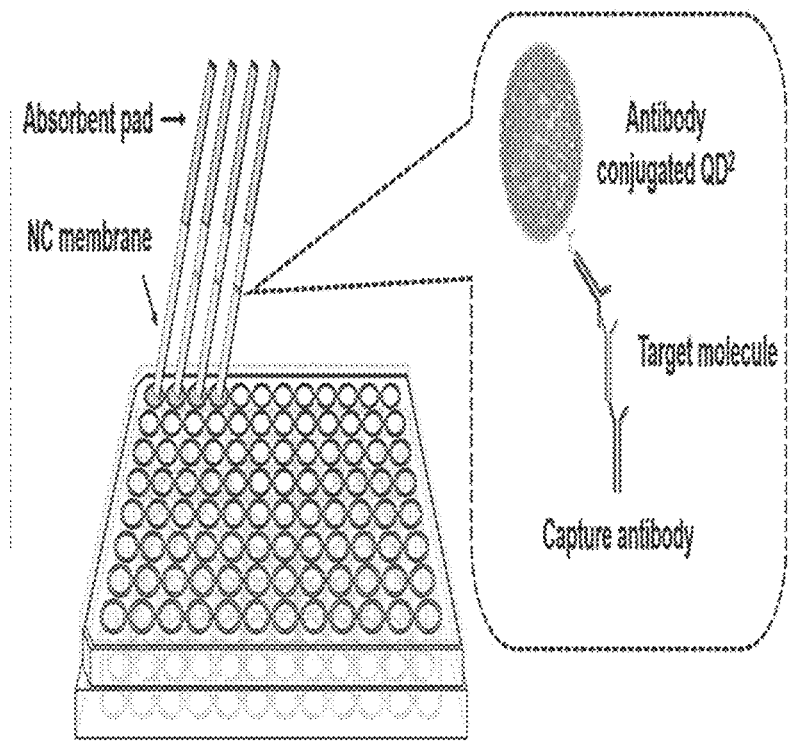
[Fig. 6A]
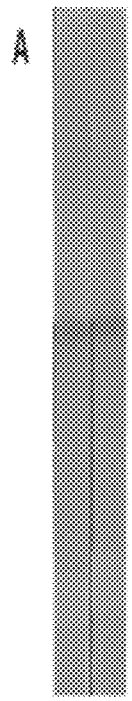

[Fig. 6B]
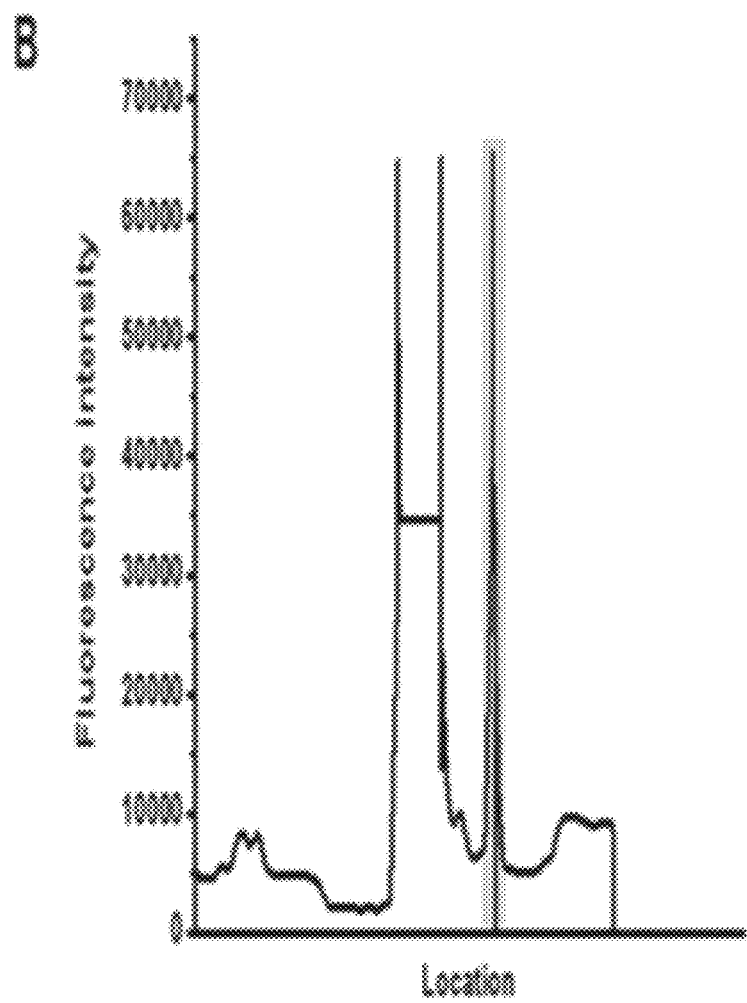

[Fig. 7]
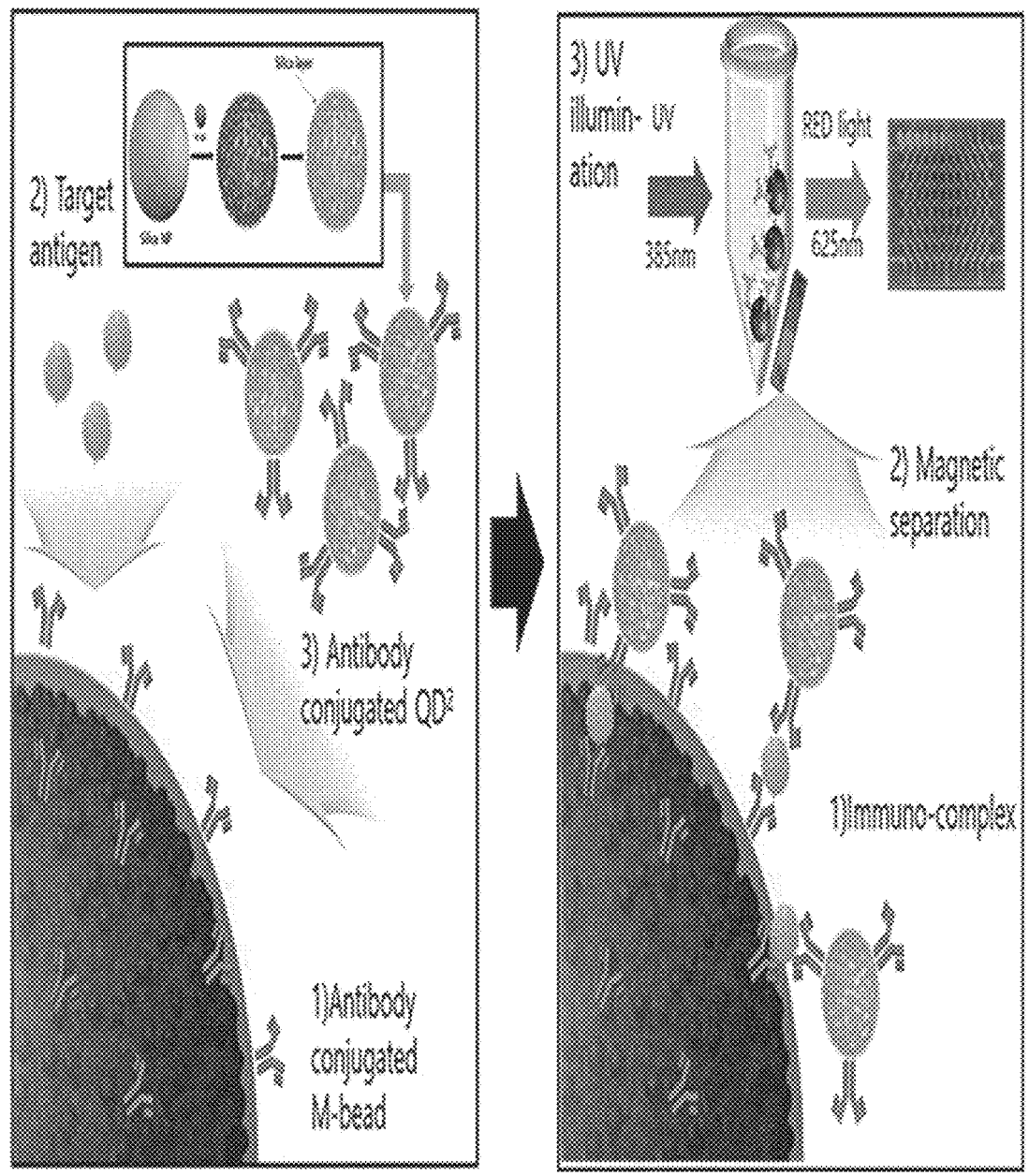

[Fig. 8A]
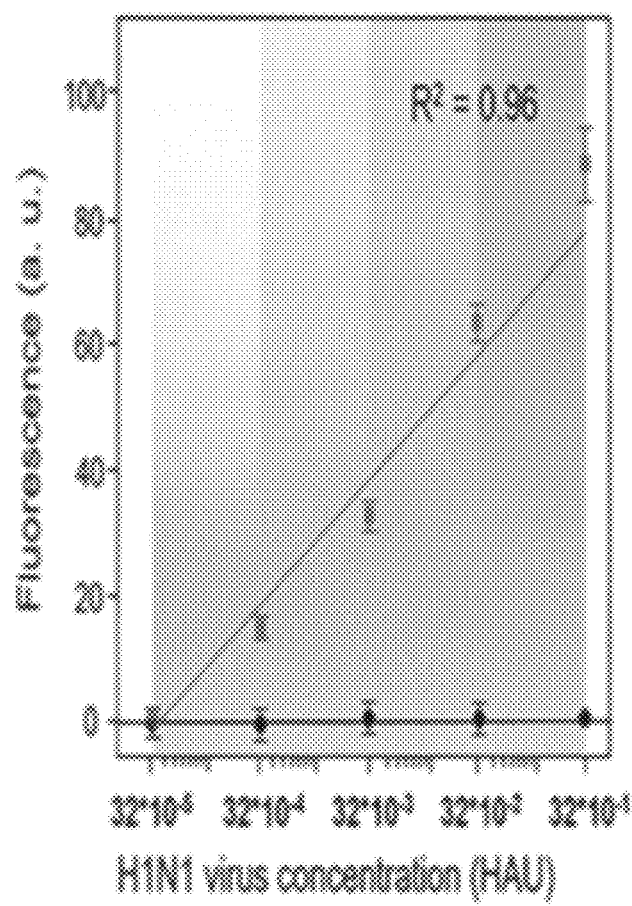

[Fig. 8B]
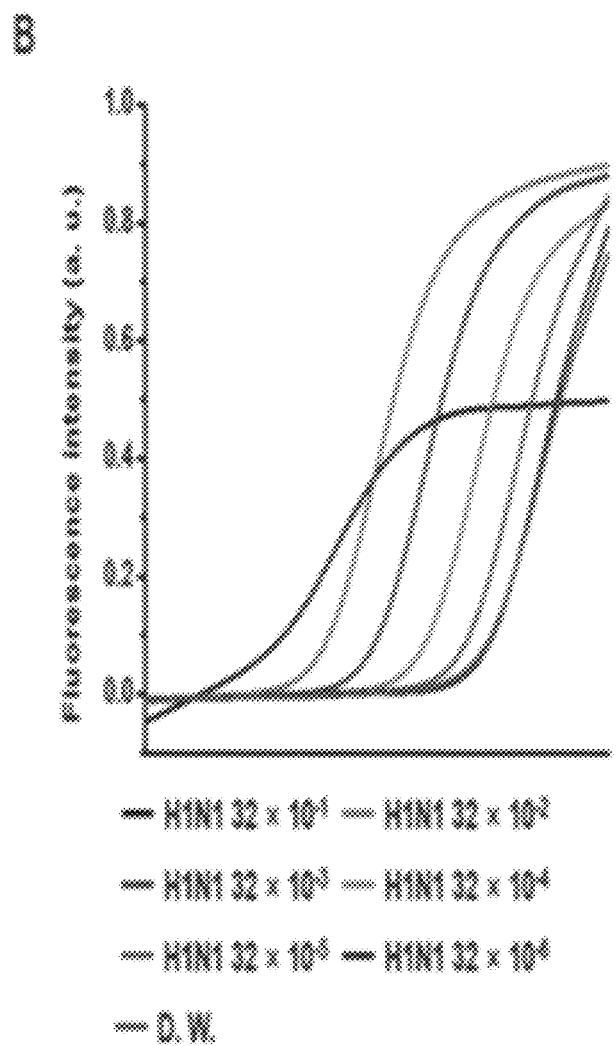

HIGHLY SENSITIVE METHODS FOR DETECTING BIOMOLECULES BASED ON MULTIPLE QUANTUM DOTS

CROSS-REFERENCE TO RELATED APPLICATIONS

This application is the U.S. National Phase under 35 U.S.C. § 371 of International Application No. PCT/KR2018/011553 filed on Sep. 28, 2018, which in turn claims the benefit of Korean Application No. 10-2017-0126515, filed on Sep. 28, 2017, the disclosures of which are incorporated by reference into the present application.

TECHNICAL FIELD

The present disclosure relates to highly sensitive methods for detecting biomolecules based on multiple quantum dots. More specifically, the present disclosure relates to bioplatforms capable of detecting biomolecules with improved quantum yield (QY) and brightness and highly sensitive methods for detecting biomolecules based on the bioplatforms.

BACKGROUND ART

With recent advances in nanoscience and nanotechnology, much research has been conducted on biodevices based on nanotechnology in bioapplications, including biotechnology, new drug development, and medical applications.

Bioplatforms are fabricated by the application of nanotechnology for superfine processing to biotechnology and immobilize biomolecules such that the biomolecules are well-ordered at a nano-level. Bioplatforms can perform their intended functions for individual molecules while preserving the activity of the biomolecules, unlike random molecular assembly. Accordingly, bioplatforms can be utilized as biosensors that require reduced amounts of samples and can be used to detect even very small amounts of target materials with good sensitivity and selectivity.

Quantum dots are considered as nanomaterials applicable to biosensors.

Quantum dots are nanomaterials that can be applied to various processes such as photoluminescence and electroluminescence. Quantum dots are spherical in shape, consist of ~5 to ~10 layers of atoms, and typically have a radius of 10 nm or less. The penetration of moisture or oxygen causes partial surface oxidation of quantum dots, and as a result, the inherent luminescent properties of the quantum dots deteriorate or disappear. Thus, capping of quantum dots, coating of quantum dots with inorganic materials, and their related technologies are currently being developed.

Particularly, coating of quantum dots with inorganic materials can stabilize the quantum dots against oxidation caused by moisture or oxygen but fails to strongly support ligands. In related technologies of single quantum dot-containing nanoparticles, for example, a silica shell serves as a simple coating layer and a considerable number of quantum dots tend to be detached during post-processing or when applied to a bioplatform.

Thus, there is a need to develop techniques for increasing the area covered by quantum dots to achieve improved quantum yield (QY) and brightness while maintaining stable bonds of the quantum dots.

DISCLOSURE

Technical Problem

The present invention has been made in an effort to overcome the above-described disadvantages and intends to provide quantum dots for bioapplications that are covered with an inorganic coating layer to achieve improved optical stability while maintaining their stable bonds.

Specifically, one object of the present invention is to provide multilayered multiple quantum dot-doped nanoparticles, each of which having a structure consisting of a core particle, a quantum dot-embedded layer, and a silica/quantum dot composite shell, and methods for producing multilayered multiple quantum dot-doped nanoparticles while maintaining a large area covered by the quantum dots and stable bonds of the quantum dots.

Another object of the present invention is to provide highly sensitive bioplatforms including the multilayered multiple quantum dot-doped nanoparticles that can be used to detect biomolecules with improved quantum yield (QY) and brightness, and highly sensitive methods for detecting biomolecules based on the bioplatforms.

Technical Solution

One aspect of the present invention provides quantum dot-doped nanoparticles, each of which includes a polymer or inorganic core particle, a quantum dot-embedded layer including a plurality of quantum dots bound to the surface of the core particle and surrounding the entire surface of the core particle, and a silica/quantum dot composite shell surrounding the quantum dot-embedded layer.

A further aspect of the present invention provides a method for producing quantum dot-doped nanoparticles, including: (a) modifying the surface of polymer or inorganic core particles with a material providing binding sites for quantum dots; (b) feeding quantum dots coated with a hydrophobic organic compound to the reaction products of step (a) and allowing the reaction to proceed to form a quantum dot-embedded layer including the quantum dots surrounding the outer surface of the core particles; (c) modifying the surface of the reaction products of step (b) with a material providing additional binding sites for unbound quantum dots; (d) supplying a base to the reaction products of step (c) and allowing the reaction to proceed to form additional binding sites for unbound quantum dots on the surface of the quantum dot-embedded layer; and (e) feeding a silanol reactant and a base to the reaction products of step (d), allowing the reaction to proceed, and purifying the resulting reaction products to form a silica/quantum dot composite shell having a structure in which a plurality of layers of the quantum dots surround the core particles.

Another aspect of the present invention provides a biological detection kit including a sensing membrane surface immobilized with quantum dot-doped nanoparticles wherein each of the quantum dot-doped nanoparticles includes a polymer or inorganic core particle, a quantum dot-embedded layer including quantum dots doped into the core particle, and a silica/quantum dot composite shell surrounding the quantum dot-embedded layer.

Another aspect of the present invention provides a bioplatform including quantum dot-doped nanoparticles and magnetic beads forming a sandwich assay structure with the quantum dot-doped nanoparticles wherein each of the quantum dot-doped nanoparticles includes a polymer or inorganic core particle, a quantum dot-embedded layer including quantum dots doped into the polymer or inorganic core particle, and a silica/quantum dot composite shell surrounding the quantum dot-embedded layer.

Another aspect of the present invention provides a biological detection method including injecting a biological sample into the bioplatform to allow the reaction to proceed and measuring the intensity of fluorescence emitted during the reaction wherein each of the quantum dot-doped nanoparticles includes a polymer or inorganic core particle, a quantum dot-embedded layer including a plurality of quantum dots bound to the surface of the core particle and surrounding the entire surface of the core particle, and a silica/quantum dot composite shell surrounding the quantum dot-embedded layer, wherein the quantum dots in the quantum dot-embedded layer surround the surface of the core particle, and wherein a plurality of layers of the surrounding quantum dots are stacked on one another.

Another aspect of the present invention provides a biological detection method including injecting a biological sample into a biological detection kit including a sensing membrane surface immobilized with quantum dot-doped nanoparticles to allow the reaction to proceed and measuring the intensity of fluorescence emitted during the reaction wherein each of the quantum dot-doped nanoparticles includes a polymer or inorganic core particle, a quantum dot-embedded layer including quantum dots doped into the core particle, and a silica/quantum dot composite shell surrounding the quantum dot-embedded layer.

Yet another aspect of the present invention provides a biological detection method including injecting a biological sample into a bioplatform including quantum dot-doped nanoparticles and magnetic beads forming a sandwich assay structure with the quantum dot-doped nanoparticles to allow the reaction to proceed and measuring the intensity of fluorescence emitted during the reaction wherein each of the quantum dot-doped nanoparticles includes a polymer or inorganic core particle, a quantum dot-embedded layer including quantum dots doped into the core particle, and a silica/quantum dot composite shell surrounding the quantum dot-embedded layer.

Advantageous Effects

Each of the multilayered multiple quantum dot-doped nanoparticles according to the present invention has a structure consisting of a polymer or inorganic core particle, a quantum dot-embedded layer, and a silica/quantum dot composite shell. The multilayered multiple quantum dot-doped nanoparticles of the present invention can be used to detect biomolecules with improved quantum yield (QY) and brightness while maintaining a large area covered by the quantum dots and stable bonds of the quantum dots. Therefore, the multilayered multiple quantum dot-doped nanoparticles of the present invention are suitable for bioapplications, including bioplatforms and highly sensitive methods for detecting biomolecules.

BRIEF DESCRIPTION OF THE DRAWINGS

FIG. 1A and FIG. 1B show schematic diagrams of a nanoparticle based on multiple quantum dots: A shows the structure of a conventional multiple quantum dot-based nanoparticle consisting of a silica core particle, a quantum dot-embedded layer, and a silica shell and B shows the structure of an inventive multilayered multiple quantum dot-based nanoparticle consisting of a silica core particle, a quantum dot-embedded layer, and a silica/quantum dot composite shell.

FIG. 2A and FIG. 2B show electron microscope images of the multiple quantum dot-based nanoparticles of FIG. 1: A shows an electron microscope image of the conventional multiple quantum dot-based nanoparticles, each having a structure consisting of a silica core particle, a quantum dot-embedded layer, and a silica shell and B shows an electron microscope image of an inventive multilayered multiple quantum dot-based nanoparticles, each having a structure consisting of a silica core particle, a quantum dot-embedded layer, and a silica/quantum dot composite shell.

FIG. 3A, FIG. 3B and FIG. 3C compare the quantum yields and brightnesses of the multiple quantum dot-based nanoparticles of FIG. 1, nanoparticles containing quantum dots modified with COOH groups as water soluble ligands (QD-COOH), conventional nanoparticles containing multiple quantum dots (single silica QD, designated by sQD), and inventive nanoparticles containing multiple quantum dots ($QD^2$, designated by mQD).

FIG. 4A, FIG. 4B and FIG. 4C show the quantum yields and brightnesses of inventive nanoparticles containing different sizes of multilayered multiple quantum dots, which were measured to investigate the possibility whether the nanoparticles can function as (multi)labeling sites.

FIG. 5 schematically shows the application of inventive multilayered multiple quantum dot-containing nanoparticles to a biomaterial detection kit and a partial enlarged diagram of the related area.

FIG. 6A and FIG. 6B show the application of inventive multilayered multiple quantum dot-containing nanoparticles to a practical biomaterial detection kit.

FIG. 7 schematically shows the application of inventive multilayered multiple quantum dot-containing nanoparticles to a sandwich assay.

FIG. 8A and FIG. 8B show the application of inventive multilayered multiple quantum dot-containing nanoparticles to a practical sandwich assay and the detection of the same target material by real-time PCR.

BEST MODE

The present invention will now be described in more detail.

The present invention provides quantum dot-doped nanoparticles, each of which includes a polymer or inorganic core particle, a quantum dot-embedded layer including a plurality of quantum dots bound to the surface of the core particle and surrounding the entire surface of the core particle, and a silica/quantum dot composite shell surrounding the quantum dot-embedded layer.

The term "quantum dot-embedded layer" as used herein refers to a layer of a plurality of quantum dots surrounding the outer surface of the core particles unless otherwise specified. The quantum dot-embedded layer is a virtual layer along a line connecting the outermost quantum dots and is defined as an interface surrounded by the silica/quantum dot composite shell.

The multilayered multiple quantum dot-containing nanoparticles of the present invention correspond to an improvement over conventional multiple quantum dot-containing nanoparticles including a quantum dot-free silica shell, so-called single quantum dot-containing nanoparticles. Due to the presence of the quantum dots in the silica/quantum dot composite shell, significantly improved quantum yield and brightness can be achieved.

According to one embodiment of the present invention, each of the quantum dot-doped nanoparticles includes a polymer or inorganic core particle, a quantum dot-embedded layer including a plurality of quantum dots bound to the surface of the core particle and surrounding the entire surface of the core particle, and a silica/quantum dot composite shell surrounding the quantum dot-embedded layer.

In the present invention, the quantum dots constituting the quantum dot-embedded layer crosslink with a silica material constituting the silica/quantum dot composite shell. This crosslinking provides a structure in which the quantum dots are randomly bound to the silica material.

The crosslinking bonds may be formed by a material providing binding sites for the quantum dots. The material providing binding sites for the quantum dots has functional groups at both ends thereof. The functional group at one end of the material is bound to the surface of the quantum dots and the functional group at the other end of the material is bound to the core particle or the silica particle constituting the silica/quantum dot composite shell.

According to the prior art, the material providing binding sites for the quantum dots is used to form a structure corresponding to the quantum dot-embedded layer. In contrast, the material providing binding sites for the quantum dots used in the present invention is also present on the surface of the quantum dot-embedded layer and provides crosslinking bonds to form the silica/quantum dot composite shell, which is different from conventional silica-only shells corresponding to multiple quantum dots or single quantum dots.

For example, the material providing binding sites for the quantum dots may have functional groups at both ends thereof. Preferably, the functional group at one end of the material is bound to the surface of the quantum dot constituting the quantum dot-embedded layer and the functional group at the other end of the material is bound to the silica material constituting the silica/quantum dot composite shell.

The functional group at one end of the material may be, for example, a silane group, a thiol group, a carbon-containing hydrophobic functional group, a carboxyl group or an amine group. The functional group at the other end of the material may be, for example, a thiol group, an amine group, an amine-containing group, an epoxy group, a halogen-containing group or a carbon-containing group.

Specific examples of the material as coupling agents having such terminal functional groups include 3-mercaptopropyltrimethoxysilane, mercaptomethyldiethoxysilane, 3-mercaptopropylmethyldimethoxysilane, 3-mercaptopropyltriethoxysilane, 2-diphenylphosphinoethyltriethoxysilane, diphenylphosphinoethyldimethylethoxysilane, 3-aminopropylmethyldiethoxysilane, 3-aminopropyldimethylethoxysilane, 3-aminopropyltriethoxysilane, 3-aminopropyltrimethoxysilane, 4-aminobutyltrimethoxysilane, 3-(m-aminophenoxy)propyltrimethoxysilane, and n-(2-aminoethyl)-3-aminopropylmethyldimethoxysilane.

The quantum dots constituting the silica/quantum dot composite shell may be, for example, those unbound to the quantum dot-embedded layer or those initially bound to but later separated from the quantum dot-embedded layer. If needed, additional quantum dots may be added and bound to the binding sites for the quantum dots.

The silica/quantum dot composite shell may be from 7 nm to 1,000 nm or from 7 nm to 300 nm in thickness. If the thickness of the silica/quantum dot composite shell is smaller than the lower limit defined above, the effect of the silica/quantum dot composite shell on the protection of the silica shell is negligible. Meanwhile, if the thickness of the silica/quantum dot composite shell exceeds the upper limit defined above, the particles become heavy and tend to settle, limiting their application.

According to the present invention, the core includes polymer core particles or inorganic core particles. The polymer core particles may be made of a stryrenic or acrylic polymer such as polystyrene or polymethyl methacrylate. The inorganic core particles may be made of silica, alumina, titanium dioxide or zinc dioxide. The core particles have a diameter of 10 nm to 100,000 nm or from 80 nm to 1,000 nm, which is preferable in terms of handling and additional post-processing. The inorganic core particles may be used as supports for quantum dots due to their good stability. In this case, since the size of the core particles is easy to control, the quantum dot-containing particles are allowed to have various sizes and a stable structure and can thus be used as fluorescent labels with various characteristics. In addition, the quantum dot-containing particles can prevent the absorption of biomolecules during bioassay to provide accurate analytical results.

Particularly, strong covalent bonds between the quantum dots and the core particles prevent the stability of the quantum dots from deterioration resulting from photobleaching and allow the luminescent properties of the quantum dots to be maintained even after long-term continuous use. The quantum dots constituting the quantum dot-embedded layer can be covalently bonded to the core particles through a material having functional groups at both ends thereof. The functional group at one end of the material contains an atom binding to the quantum dot and the functional group at the other end of material is bound to the core particle. The atom may be selected from sulfur, nitrogen, and phosphorus atoms. The functional group at the other end of the material may be a silane, amino, sulfone, carboxyl or hydroxy group.

The quantum dots may have a single core structure composed of a Group II-VI, Group III-V or Group IV-IV semiconductor or a core/cap structure in which the single core structure is capped with a Group II-IV semiconductor. The quantum dot-containing nanoparticles may have a diameter of 1 nm to 50 nm or 1 nm to 20 nm. Here, the quantum dots corresponding to the single core or the core of the core/cap structure may be composed of any type of semiconductor. For example, the Group II-VI semiconductor may consist of at least one of the Group IIB elements and at least one of the Group VIB elements in the periodic table. Examples of such Group II-VI semiconductors include CdS, CdSe, CdTe, ZnSe, ZnS, PbS, PbSe, HgS, HgSe, HgTe, CdHgTe, and $CdSe_xTe_{1-x}$. Examples of such Group III-V semiconductors include GaAs, InAs, and InP. The Group II-VI semiconductor is preferably used as the core material and its diameter is from 1 nm to 20 nm or from 2 nm to 10 nm.

In the core/cap structure, the cap is composed of semiconductor quantum dots that bind to the core semiconductor quantum dots to form a coating layer on the surface of the core semiconductor. The core/cap structure ensures a higher quantum yield of nanoparticles than the single core structure. The cap has a higher band gap than the core semiconductor and serves as a passivation layer to protect the core semiconductor from the external environment. The cap is composed of a Group II-VI semiconductor with a high band gap, preferably ZnS, CdS or ZnSe. The core/cap structure may use various combinations of the semiconductors. For example, the core may be composed of CdSe or CdS and the cap may be composed of ZnS. Alternatively, the core may be composed of CdSe and the cap may be composed of CdSe or ZnSe. The semiconductors can be combined without limitation.

The quantum dots may be of type I. The type I quantum dots may have a structure consisting of a Group 12-16 semiconductor core and a Group 12-16 semiconductor shell, for example, a cadmium selenide (CdSe) core and a zinc sulfide (ZnS) shell capping the core. For reference, capping of core particles having a low band gap with shells having a high band gap was demonstrated to achieve improved luminescent properties. For example, when CdSe quantum dots are capped with a ZnS layer, strong luminescent properties (quantum yields 35-50%) are attained at room temperature. The controlled size of the powder enables control over the emission wavelength from blue to red. Furthermore, the ZnS capping protects the surface of the core to ensure good stability of the quantum dots.

The quantum dot-embedded layer may be formed by multiple doping of the quantum dots coated with a hydrophobic organic compound on the outer surface of the core particles. The doped quantum dots form layers sequentially surrounding the core particles. The number of the quantum dots constituting the quantum dot-embedded layer may be from 1 to 400,000, from 1 to 4,000 or from 400 to 500.

The silica/quantum dot composite shell may consist of a plurality of layers that are formed on the outer surface of the quantum dot-embedded layer to sequentially surround the quantum dot-embedded layer. For example, the number of the quantum dots present in the silica/quantum dot composite shell may be from 10 to 100,000 or from 200 to 5,000.

The layer density of the quantum dots in the silica/quantum dot composite shell is in the range of 0.00001 to 99.99999%, preferably 30 to 90%, more preferably 70 to 80%, based on the imaginary surface area of the quantum dot-embedded layer. The density is calculated by using the formula of density (density=mass/volume). Within this range, the quantum yield and brightness of the multilayered multiple quantum dot-containing nanoparticles can be improved.

The multilayered multiple quantum dot-containing nanoparticles of the present invention may further include a silica-based shell surrounding the silica/quantum dot composite shell. The silica-based shell can provide a stable templet when combined with alumina, titanium dioxide or zinc dioxide. The use of this stable templet facilitates control over the size of the multilayered multiple quantum dot-containing nanoparticles and enables centrifugation and washing of the multilayered multiple quantum dot-containing nanoparticles.

One of the multiple quantum dot-based nanoparticles is schematically shown in B of FIG. 1. Referring to B of FIG. 1, the structure of the multilayered multiple quantum dot-based nanoparticle consists of the silica core particle, the quantum dot-embedded layer, and the silica/quantum dot composite shell. As will be specifically discussed below, the material providing binding sites for the quantum dots is first supplied for crosslinking and a base such as ammonium hydroxide, sodium hydroxide, potassium hydroxide, calcium hydroxide or magnesium hydroxide is then supplied. According to this procedure, the functional group at one end of the material providing binding sites for the quantum dots is bound to the surface of the quantum dots constituting the quantum dot-embedded layer and the other terminal functional group can be provided as a site that is bound with the silica material constituting the silica/quantum dot composite shell. The base provides binding sites for additional quantum dots. These are technical features of the present invention.

The multilayered multiple quantum dot-containing nanoparticles of the present invention are characterized by the formation of the silica/quantum dot composite shell. The multilayered multiple quantum dot-containing nanoparticles show uniform, high fluorescence signals compared to conventional quantum dot-containing nanoparticles.

A of FIG. 1 shows the structure of a conventional multiple quantum dot-based consisting of a silica core particle, a quantum dot-embedded layer, and a silica shell. In a conventional method for producing single quantum dot-containing nanoparticles including a quantum dot-free silica shell as a simple coating layer, a material providing binding sites for quantum dots and a base are supplied simultaneously to provide crosslinking bonds between quantum dots and the silica-only shell. Accordingly, the conventional method fails to provide the multilayered multiple quantum dot-containing nanoparticles of the present invention.

FIG. 2 shows electron microscope images of the multiple quantum dot-based nanoparticles of FIG. 1. Specifically, A of FIG. 2 shows conventional multiple quantum dot-based nanoparticles, each having a structure consisting of a silica core particle, a quantum dot-embedded layer, and a silica shell and B of FIG. 2 shows the inventive multilayered multiple quantum dot-based nanoparticles, each having a structure consisting of a silica core particle, a quantum dot-embedded layer, and a silica/quantum dot composite shell.

The layer density of the quantum dots on the surface of the quantum dot-embedded layer may be more than 5% or more than 20%, as determined by the proportion of the surface area of the quantum dots in the surface area of the core particles. In the present invention, the layer density of the quantum dots on the surface of the silica/quantum composite shell may be more than 10% or more than 60%, as determined by the proportion of the surface area of the quantum dots in the (imaginary) surface area of the quantum dot-embedded layer. As can be seen from the Examples section that follows, the introduction of thiol groups capable of strong binding to the surface of the core enables the embedding of the quantum dots along the outer surface of the core when not sterically hindered (formation of the quantum dot-embedded layer). Since there is no need to introduce a single layer of the quantum dots on the surface of the core, the silica/quantum dot composite shell can induce the introduction of a greater number of the quantum dots.

A method for producing the multilayered multiple quantum dot-containing nanoparticles can be carried out as follows but is not limited thereto.

First, in step (a), the surface of polymer or inorganic core particles is modified with a material providing binding sites for quantum dots. Specifically, the material providing binding sites for quantum dots is allowed to react with the core particles to prepare a core on which surface binding sites for quantum dots are created.

In subsequent step (b), quantum dots coated with a hydrophobic organic compound are fed to the reaction products of step (a) and the reaction is allowed to proceed to form a quantum dot-embedded layer including the quantum dots surrounding the outer surface of the core particles. Then, a hydrophobic organic solvent is fed to the reaction products of step (b) and the reaction is allowed to proceed to bind unbound quantum dots to the binding sites for the quantum dots on the core surface. Thereafter, it is preferable to stabilize the reaction. For example, a hydrophobic solvent such as dichloromethane, dichloroethane, a benzene-based solvent (for example, benzene, toluene, chlorobenzene or ethylbenzene) or an alkyl chain solvent (for example, hexane, heptane or cyclohexane) is added and stirred for about 30 seconds to about 60 seconds for sufficient binding of the quantum dots to provide nanoparticles including the quantum dot-embedded layer.

In subsequent step (c), the surface of the reaction products of step (b) is modified with a material providing additional binding sites for unbound quantum dots. Specifically, the material providing additional binding sites for unbound quantum dots is fed to the reaction products of step (b) and the reaction is allowed to proceed such that the functional group at one end of the material is bound to the surface of the quantum dots constituting the quantum dot-embedded layer and the functional group at the other end of the material is provided as a site that is bound with a silica material constituting the silica/quantum dot composite shell.

In step (d), a base is supplied to the reaction products of step (c), the reaction is allowed to proceed to form additional binding sites for unbound quantum dots on the surface of the quantum dot-embedded layer.

Thereafter, in step (e), a silanol reactant and a base are fed the reaction products of step (d), the reaction is allowed to proceed, and the resulting reaction products are purified to form a silica/quantum dot composite shell having a structure in which a plurality of layers of the quantum dots surround the core particles.

Steps (c) and (d) may be repeated a certain number of times as required. Steps (c) and (d) are preferably repeated 3-4 times. In this case, a 20-500 nm thick silica/quantum dot composite shell can be formed.

As described above, the silica/quantum dot composite shell is formed by a suitable process for stacking and coating a plurality of layers of the quantum dots. For example, quantum dots and 3-mercaptopropyltrimethoxysilane (MPTS) as a material providing binding sites for the quantum dots are first fed, a base is then fed such that unbound quantum dots to the quantum dot-embedded layer or quantum dots initially bound to but later separated from the quantum dot-embedded layer are bound to the binding sites for the quantum dots and are incorporated in the silica shell. For reference, when MPTS and the base are added together with quantum dots, a monolayer coating is provided, as shown in A of FIG. 1.

According to the method of the present invention, the quantum dots, the core particles, and the material providing binding sites are in a volume ratio of 1:0.000001-60: 0.000001-890, preferably 1:0.01-20:0.01-300, more preferably 1:1-2:2-3.

The core particles, the quantum dot-embedded layer, and the silica/quantum dot composite shell are in a thickness ratio of 1:0.1-9:1-10, preferably 1:0.4-4:1-4, more preferably 1:1-2:1-2.

The layer density of the quantum dots in the silica/quantum dot composite shell is in the range of 0.00001 to 99.99999%, preferably 30 to 90%, more preferably 70 to 80%, based on the imaginary surface area of the quantum dot-embedded layer. The density is calculated by using the formula of density (density=mass/volume).

The resulting multilayered multiple quantum dot-containing nanoparticles are structured such that the plurality of quantum dots are stably bound to the surface of the core particles and are also present in the shell. This structure can maximize the number of the quantum dots in the multilayered multiple quantum dot-containing nanoparticles. Furthermore, even when different sizes of the quantum dots are used, the multilayered multiple quantum dot-containing nanoparticles provide a quantum yield and a brightness sufficient to observe the colors of light emitted depending on the size of the quantum dots. Due to this advantage, the multilayered multiple quantum dot-containing nanoparticles can function as (multi)labeling sites when used in bioapplications.

FIG. 3 compares the quantum yields and brightnesses of the multiple quantum dot-based nanoparticles of FIG. 1, nanoparticles containing quantum dots modified with COOH groups as water soluble ligands (QD-COOH), conventional nanoparticles containing multiple quantum dots (single silica QD, designated by sQD), and the inventive nanoparticles containing multiple quantum dots ($QD^2$, designated by mQD). The QYs of the QD-COOH (Control), the silica coated QD, and the multilayered quantum dot-containing nanoparticles ($QD^2$) can be seen from A of FIG. 3. The fluorescence intensities of the single QD and the multilayered quantum dot-containing nanoparticles can be seen from B of FIG. 3. The single QD and the multilayered quantum dot-containing nanoparticles were visually observed using a UV lamp at 365 nm (C of FIG. 3).

FIG. 4 shows the quantum yields and brightnesses of the inventive nanoparticles containing different sizes of multilayered multiple quantum dots, which were measured to investigate the possibility whether the nanoparticles can function as (multi)labeling sites. As can be seen from FIG. 4, the inventive multilayered multiple quantum dot-containing nanoparticles had improved quantum yield and brightness and displayed different emission and fluorescence colors depending on the size of the quantum dots used. Therefore, the inventive multilayered multiple quantum dot-containing nanoparticles can be effectively used for bioapplications, including bioplatforms. That is, the inventive multilayered multiple quantum dot-containing nanoparticles possess high sensitivity at a level comparable to that of real-time PCR, enabling precise and rapid diagnosis of new infectious pathogens where ultrahigh sensitivity is required. In addition, the inventive multilayered multiple quantum dot-containing nanoparticles enable parallel analysis of biomarkers at different concentrations due to their broad dynamic range ($\geq$log 10).

As a specific example of the bioapplications, the present invention provides a biological detection kit including a sensing membrane surface immobilized with quantum dot-doped nanoparticles wherein each of the quantum dot-doped nanoparticles includes a polymer or inorganic core particle, a quantum dot-embedded layer including quantum dots doped into the core particle, and a silica/quantum dot composite shell surrounding the quantum dot-embedded layer.

For example, the quantum dot-doped nanoparticles may be immobilized on the sensing membrane by dehydration-condensation.

For example, the sensing membrane may be formed on a glass plate, a polystyrene plate or a microtiter plate.

For example, the biological detection kit may be used to detect a material selected from the group consisting of monosaccharides, polysaccharides, organic acids, alcohols, cholesterol, choline, xanthine, and mixtures thereof.

The use of the biological detection kit is explained with reference to FIG. 5. FIG. 5 schematically shows the application of the inventive multilayered multiple quantum dot-containing nanoparticles to the biomaterial detection kit and a partial enlarged diagram of the related area. The practical application of the multiple quantum dot-containing nanoparticles to the kit is shown in FIG. 5. The partial enlarged diagram explains the reactions of the antibody-conjugated multiple quantum dot-containing nanoparticles, a target material, and a capture antibody in the red lines on nitrocellulose (NC) membranes of the kit.

As another specific example, magnetic beads may be applied to a sandwich assay. In this case, a magnet may be used to retrieve a bioplatform in a simple manner. The term "bioplatform" as used herein refers to a platform that is used for molecular diagnosis such as immunodiagnosis unless otherwise specified. The bioplatform can provide the shell surface of the multilayered multiple quantum dot-containing nanoparticles as a (multi)labeling site.

The multilayered multiple quantum dot-containing nanoparticles included in the bioplatform may use various sizes of the quantum dots. Thus, the multilayered multiple quantum dot-containing nanoparticles can function as (multi) labeling sites due to their ability to provide different luminescence intensities with improved efficiency and brightness for different target materials even when used in a very small amount.

As an example, an antibody complementarily binding to a target material (biological sample) may be conjugated to the multilayered multiple quantum dot-containing nanoparticles such that the conjugated antibody captures the biological sample (target material).

As a specific example, a structure may be provided in which the multilayered multiple quantum dot-containing nanoparticles are modified with a suitable ligand, an antibody complementarily binding to a target material (biological sample) is conjugated to the multilayered multiple quantum dot-containing nanoparticles, and the conjugated antibody captures the biological sample (target material). The ligand may be any of those known in the art, for example, a receptor-ligand pair capable of inducing receptor-ligand interactions, such as streptavidin-biotin, avidin-biotin or asialoglycoprotein-galactose.

The biological sample (target material) may be, for example, selected from the group consisting of antigens, receptors, viruses, enzymes, infectious immunoglobulins, cytokines, and other infectious factors.

The biological sample (target material) can provide a sandwich assay structure captured with magnetic beads for subsequent stable emission measurement. In this case, the magnetic beads include an antibody complementarily binding to a biological sample (target material) and the antibody conjugated to the magnetic beads captures the biological sample (target material) independently of the antibody conjugated to the multilayered multiple quantum dot-containing nanoparticles. As a specific example, a structure may be provided in which the magnetic beads are modified with a suitable ligand for complementarily binding an antibody to a target material (biological sample), the antibody is conjugated to the magnetic beads, and the conjugated antibody captures the biological sample (target material). The ligand may be a receptor-ligand pair capable of inducing receptor-ligand interactions, such as streptavidin-biotin, avidin-biotin or asialoglycoprotein-galactose.

As a related specific example, a bioplatform of the present invention includes quantum dot-doped nanoparticles and magnetic beads forming a sandwich assay structure with the quantum dot-doped nanoparticles wherein each of the quantum dot-doped nanoparticles includes a polymer or inorganic core particle, a quantum dot-embedded layer including quantum dots doped into the polymer or inorganic core particle, and a silica/quantum dot composite shell surrounding the quantum dot-embedded layer.

The magnetic beads may have a diameter ranging from 1 to 5 which is suitable for the separation and purification of samples. The magnetic beads may be made of a high molecular weight polymer containing a magnetic material. The outer surface of the magnetic beads may be surrounded by a silica shell. The silica shell protects the magnetic beads and its surface may be modified with a variety of ligands for assay. For example, the magnetic beads may be made of a copolymer prepared by copolymerization of a mixture of polystyrene seeds and a styrene monomer with a styrene derivative in the presence of an emulsifier and an oil soluble peroxide polymerization initiator. In the magnetic poly (styrene-co-styrene derivative) copolymer, sulfonic acid functional groups are introduced into styrene rings constituting the backbone and iron ions are bonded to the sulfonic acid functional groups. A silica shell surrounds the outer surface of the copolymer beads. The use of the poly(styrene-co-styrene derivative) copolymer is preferred because of its ability to prevent non-specific binding.

As a specific example, the magnetic beads may be prepared in the following order.

First, in step a), a styrene monomer is subjected to emulsifier-free emulsion polymerization in the presence of a dispersion stabilizer and a radical initiator to prepare polystyrene seeds.

In step b), the polystyrene seeds are pre-swollen in the presence of a plasticizer such as dibutyl phthalate.

In step c), a mixture of the pre-swollen polystyrene seeds and a styrene monomer is subjected to aqueous dispersion copolymerization with a styrene derivative in the presence of an emulsifier and an oil soluble peroxide polymerization initiator to prepare poly(styrene-co-divinylbenzene) copolymer beads.

In step d), the poly(styrene-co-divinylbenzene) copolymer beads are allowed to react with a sulfonation agent, and prepared poly(styrene-co-divinylbenzene) copolymer beads including sulfuric acid functional group. As a specific example, the sulfonation agent may be selected from chlorosulfonic acid, acetyl sulfate, and concentrated sulfuric acid and the reaction may be carried out in the temperature range of 60 to 95° C.

In step e), the poly(styrene-co-divinylbenzene) copolymer beads including sulfonic acid functional groups are magnetized with a superparamagnetic iron precursor. As a specific example, the magnetization is performed using a mixture of ferrous chloride ($FeCl_2$) and ferric chloride ($FeCl_3$). The molar ratio of $FeCl_2.4H_2O:FeCl_3.6H_2O$ in the mixture may be 1:500-10,000 or 1:1-2.

Then, in step f), a silica shell is formed to surround the outer surface of the magnetic poly(styrene-co-divinylbenzene) copolymer beads.

A biological detection method using the bioplatform can be carried out as follows.

First, a biological sample (target material) is injected into the bioplatform including the quantum dot-doped nanoparticles and the magnetic beads forming a sandwich assay structure with the quantum dot-doped nanoparticles, the reaction is allowed to proceed, and the intensity of fluorescence emitted during the reaction is measured.

As described above, each of the quantum dot-doped nanoparticles may include a polymer or inorganic core particle, a quantum dot-embedded layer including quantum dots doped into the core particles, and a silica/quantum dot composite shell surrounding the quantum dot-embedded layer.

The quantum dot-doped nanoparticles constituting the bioplatform may use various sizes of the quantum dots.

Thus, the shell surface of each of the nanoparticles may function as a (multi)labeling site for a biological sample(s).

The fluorescence intensity may be measured by an optical method or an electrical signal converted from the fluorescence intensity may be measured. However, there is no restriction on the method for measuring the fluorescence intensity.

The use of the bioplatform will be described with reference to FIG. 7. FIG. 7 schematically shows the application of the inventive multilayered multiple quantum dot-containing nanoparticles to a sandwich assay.

Referring to FIG. 7, the multilayered multiple quantum dot-containing nanoparticles (or the magnetic beads) are added to an aqueous solution or organic solvent containing the biological sample (target material), a solution is prepared in which an antibody conjugated to the multilayered multiple quantum dot-containing nanoparticles or an antibody conjugated to the magnetic beads is bound to one side of the biological sample (target material), and the magnetic beads (or the multilayered multiple quantum dot-containing nanoparticles) are added to the solution.

Then, a solution having a platform structure is prepared in which the biological sample (target material) bound with the antibody conjugated to the multilayered multiple quantum dots is bound with the antibody conjugated to the magnetic beads or is bound with the antibody conjugated to the magnetic beads and then the antibody conjugated to the multilayered multiple quantum dots is bound thereto.

Subsequently, a magnetic material is brought into the solution to collect the magnetic beads and the absorbance or fluorescence intensity of the quantum dots present in the quantum dot-containing particles in the area where the magnetic beads are collected.

The target material-containing solution may be, for example, a solution for myocardial infarction multiple assay, infectious immunoglobulin parallel diagnosis, cytokine parallel diagnosis or blood screening.

The present invention will be explained in more detail with reference to the following examples. However, these examples are intended to merely illustrate specific embodiments of the present invention and should not be construed as limiting or restricting the present invention.

EXAMPLES

Example 1: Preparation of Multilayered Multiple Quantum Dot-Containing Quantum Dots <Core Particles>

Silica particles with a diameter of 120 nm (10 mg/ml) were prepared by the Stöber method.

<Quantum Dot-Embedded Layer>

10 μl of 1% (v/v) 3-mercaptopropyltrimethoxysilane (MPTS) as a material providing binding sites for quantum dots was added to the core particles. The mixture was stirred at 25° C. for 12 h to introduce thiol groups on the surface of the core particles.

Fluorescence emitting quantum dots were bound to the outer surface of the thiol group-introduced core particles by the following procedure.

7 mg of solid-state quantum dots (CdSe/ZnS, 10 nm) coated with oleic acid as a hydrophobic organic compound were added to the thiol group-introduced core. The mixture was vigorously vortex-stirred. As a result, the quantum dots were bound to the thiol groups introduced on the core surface to form a quantum dot-embedded layer while making the core hydrophobic. Subsequently, 4 mL of dichloromethane as a hydrophobic solvent was added, followed by stirring for additional 30-60 sec to bind unbound quantum dots to the thiol groups.

Subsequently, 50 μl of mercaptopropyltriethoxysilane (MPTES) as a material providing for binding of quantum dots was added, stirred for 15 min, added with 50 μl of 25% ammonium hydroxide ($NH_4OH$ (aq)) as a base, and stirred for additional 15 min to form a quantum dot-embedded layer structure surrounding the outer surface of the core particles and having surface binding sites for additional quantum dots.

<Composite Shell/Multilayered Multiple Quantum Dot-Containing Nanoparticles>

The structures having binding sites for additional quantum dots on the surface of the quantum dot-embedded layer were washed three times with ethanol. 50 μl of tetraethyl orthosilicate as a silanol reactant and 25% ammonium hydroxide as a base were stirred at 68 rpm for 20 h and washed three times with ethanol to form a silica/quantum dot composite shell consisting of a silica shell and multiple quantum dots present in the silica shell.

The structures of the silica core, the quantum dot-embedded layer, and the silica/quantum dot composite shell are schematically shown in B of FIG. 1. As can be seen from B of FIG. 1, the multilayered multiple quantum dots were randomly embedded in the shell of each layer. An electron microscopy image of the multilayered multiple quantum dot-containing nanoparticles, each having a structure consisting of the silica core, the quantum dot-embedded layer, and the silica/quantum dot composite shell, is shown in B of FIG. 2. As can be seen from B of FIG. 2, the structure was multilayered. The layer density of the quantum dots in the silica/quantum dot composite shell was 70 to 80% in the range of 0.00001 to 99.99999%, based on the imaginary surface area of the quantum dot-embedded layer. The density was calculated by using the formula of density (density=mass/volume).

Comparative Example 1: Preparation of Multiple Quantum Dot-Containing Nanoparticles Multiple quantum dot-containing nanoparticles were prepared in the same manner as in Example 1, except that 50 μl of mercaptopropyltriethoxysilane (MPTES) and 50 μl of 25% ammonium hydroxide ($NH_4OH$ (aq)) as a base were added simultaneously, rather than sequentially as in the section <Quantum dot-embedded layer>. As a result, a silica-only shell containing multiple quantum dots was formed.

The structures of the silica core, the quantum dot-embedded layer, and the silica shell are schematically shown in A of FIG. 1. As can be seen from A of FIG. 1, the multiple quantum dots were randomly embedded in the single-layer shell. An electron microscopy image of the multiple quantum dot-containing nanoparticles, each having a structure consisting of the silica core, the quantum dot-embedded layer, and the silica shell, is shown in A of FIG. 2. As can be seen from A of FIG. 2, the structure was single-layered.

Experimental Example 1

The quantum yields and brightnesses of the multiple quantum dot-containing nanoparticles prepared in Example 1 and Comparative Example 1 were measured. The results are summarized in FIG. 3. FIG. 3 compares the quantum yields and brightnesses of nanoparticles containing quantum dots modified with COOH groups as water soluble ligands (QD-COOH), the multiple quantum dot-containing nanoparticles prepared in Comparative Example 1 (single silica QD, designated by sQD), and the multiple quantum dot-containing nanoparticles prepared in Example 1 ($QD^2$, designated by mQD). The QYs of the QD-COOH (Control), the silica coated QD, and the multilayered quantum dot-containing nanoparticles ($QD^2$) can be seen from A of FIG. 3. The fluorescence intensities of the single QD and the multilayered quantum dot-containing nanoparticles can be seen from B of FIG. 3. The single QD and the multilayered quantum dot-containing nanoparticles were visually observed using a UV lamp at 365 nm (C of FIG. 3).

Example 2

In this example, the possibility whether the nanoparticles containing different sizes of multilayered multiple quantum dots can function as (multi)labeling sites were investigated.

Specifically, the multilayered quantum dot-containing nanoparticles prepared in Example 1 were defined as Red color $QD^2$. Multilayered quantum dot-containing nanoparticles were prepared in the same manner as in Example 1, except that the size of the quantum dots was changed to 2 nm, 2.5 nm, and 3 nm. These multilayered quantum dot-containing nanoparticles were defined as Blue color $QD^2$, Green color $QD^2$, and Yellow color $QD^2$, respectively.

FIG. 4 shows the quantum yields and brightnesses of the multilayered quantum dot-containing nanoparticles of different colors. Specifically, A of FIG. 4 shows the QY of the multilayered quantum dot-containing nanoparticles. B of FIG. 4 shows the normalized fluorescence intensities of the multilayered quantum dot-containing nanoparticles. The multilayered quantum dot-containing nanoparticles were visually observed using a UV lamp at 365 nm (C of FIG. 4).

Application Example 1: Biological Detection Kit

The application of the multilayered multiple quantum dot-containing nanoparticles to a biological detection kit is explained with reference to FIG. 5. FIG. 5 schematically shows the application of the inventive multilayered multiple quantum dot-containing nanoparticles to a biomaterial detection kit and a partial enlarged diagram of the related area.

<Surface Modification of the Multilayered Multiple Quantum Dot-Containing Nanoparticles>

1 mg of the multilayered multiple quantum dot-containing nanoparticles prepared in Example 1 were added to (3-aminopropyl)triethoxysilane (APTS solution, 5% v/v, 1 mL) and stirred at room temperature for 1 h. Thereafter, the mixture was washed three times with ethanol, and 75 mg of succinic anhydride, 500 µl of a 2-methyl-2-pyrrolidone (NMP) solution, and 3.50 µl of N,N-diisopropylethylamine (DIEA) were added thereto. The resulting mixture was stirred for 2 h.

Subsequently, the reaction mixture was washed three times with dimethylformamide (DMF), and 100 µl of dimethylpyridine (DMP) and 2.1 mg of 4-dimethylaminopyridine (DMAP) were added thereto. The mixture was added with 27 µl of DIC and stirred at room temperature for 1 h. The reaction mixture was washed twice with 2-methyl-2-pyrrolidone (NMP), once with trisphosphate buffer solution (TPBS), and once with phosphate buffer solution (PBS, pH 7.2), and was dispersed in phosphate buffer solution (PBS, pH 7.2) to modify the surface of the multilayered multiple quantum dot-containing nanoparticles for antibody conjugation.

<Antibody Conjugation>

10 pmoles of an antibody was added to 100 µg of the surface-modified multilayered quantum dot-containing nanoparticles and shaken at room temperature for 2 h. Subsequently, the reaction products were washed four times with PBS (pH 7.2), a bovine serum albumin (BSA) solution (5% w/w, 1 mL) was added to the antibody-conjugated multilayered quantum dot-containing nanoparticles, followed by shaking at room temperature for 1 h.

A kit was constructed and used for antigen capture, as shown in FIG. 6. FIG. 6 shows the application of the inventive multilayered multiple quantum dot-containing nanoparticles to a practical biomaterial detection kit. As can be seen from A of FIG. 6, a captured antigen was bound to a capture antibody and a target material at the line on the absorbent pad where the capture antibody resided. The fluorescence intensity at the line in the kit was observed using a kit analyzer (B of FIG. 6).

Application Example 2: Sandwich Assay

A sandwich assay was conducted for an antigen using multilayered quantum dot nanoparticles prepared in the same manner as in Example 1 and antibody-conjugated magnetic beads, as shown in FIG. 7.

The magnetic beads were prepared by the following procedure.

<Preparation of Magnetic Beads>
<Polystyrene Seeds>

Monodisperse macroporous polystyrene-divinylbenzene beads were prepared by seeded polymerization. Specifically, monodisperse polystyrene seeds (4 µm) were prepared using dispersion polymerization method. Dispersion medium was ethanol/2-methoxyethanol (3:2, v/v) which contains 1 g of polyvinylpyrrolidone-40 (PVP-40) as a steric stabilizer (90 mL).

Azobisisobutyronitrile (AIBN, 150 mg) was dissolved in styrene (15 mL) in which inhibitor was removed and then was added to the as-prepared dispersion medium. After surface treatment for 10 min, dispersion polymerization was performed in a cylindrical reaction chamber with shaking (120 cpm) at 70° C. for 20 h. The suspension was centrifuged and the precipitates were washed with distilled water. The resulting polystyrene seeds were washed with ethanol and dried under vacuum overnight, affording polystyrene seeds (4 µm, 8.3 g).

<Polymerization of Monodisperse Macroporous Polystyrene-Co-DVB>

The polystyrene seeds (4 µm, 700 mg) were dispersed in dibutyl phthalate (DBP, 0.7 mL) emulsified aqueous medium (100 mL) containing 0.25% (w/w) sodium dodecyl sulfate (SDS) in a glass reactor equipped with an overhead stirrer and a reflux condenser. The resulting dispersion medium was stirred at 400 rpm at room temperature for 20 h, the polystyrene seeds were allowed to swell in a DBP mixture of BP (240 mg) in styrene (4.6 mL) and divinylbenzene (DVB, 2.3 mL), and dipped in 100 mL of an aqueous medium containing 0.25% (w/w) sodium dodecyl sulfate (SDS) by using a homogenizer for 1 min. The corresponding emulsified monomer solution was added to the dibutyl phthalate (DBP)-swollen polystyrene seeds dispersion medium with stirring.

<Preparation of Macroporous PS-DVB Beads>

Monomer swelling was performed for 20 h at room temperature with continuous stirring at 400 rpm. After swelling process, an aqueous solution of 10% (w/v) polyvinyl alcohol (PVA) in distilled water (10 mL) was added to the dispersion medium and the medium was purged with nitrogen stream for 30 min. The seeded polymerization was performed at 70° C. for 20 h with continuous stirring at 200 rpm to obtain monodisperse PS-DVB beads.

The obtained beads were washed, centrifuged, and washed with deionized water (50° C.). Subsequently, the collected beads were washed with ethanol and tetrahydrofuran (THF) to remove dibutyl phthalate (DBP) and linear polymer. Finally, the beads were dried under vacuum at 30° C. for 24 h to obtain macroporous PS-DVB beads (7.5 μm, 2.5 g).

<Sulfonation of Macroporous PS-DVB Beads>

The obtained macroporous PS-DVB beads (1 g) were added to 5 mL of acetic acid in an ice bath. Sulfuric acid (50 mL) was then slowly added to the beads at room temperature and the temperature was increased up to 90° C. and the resin mixture was stirred for 30 min to 2 h. The dispersion was poured into iced water (400 mL) to quench the reaction and the sulfonated PS-DVB beads were collected by centrifugation. The beads were extensively washed with deionized water by repeating centrifugation. Subsequently, the sulfonated beads were washed three times with ethanol and dried under vacuum (1.1 g).

<Magnetization of Sulfonated Macroporous PS-DVB Beads>

The sulfonated macroporous PS-DVB beads (500 mg) were dispersed in deionized water (10 mL) at room temperature with mechanical stirring (200 rpm) and purging with nitrogen. A freshly prepared mixture of $FeCl_3 \cdot 6H_2O$ (618 mg, 2.26 mmol) and $FeCl_2 \cdot 4H_2O$ (257 mg, 1.28 mmol) in deionized water (10 mL) was added to the dispersion for adsorption.

After 2 h, with continuous stirring 28% ammonium hydroxide (50 mL) was added dropwise to the beads suspension for 40 min. The magnetized macroporous beads were isolated from the mixture by centrifugation, washed with 25% trifluoroacetic acid (TFA), and then washed with deionized water and ethanol. Finally, the magnetized macroporous beads were dried under vacuum (7.5 μm, 653 mg).

<Shell>

A (3-aminopropyl)triethoxysilane solution (1% (v/v), 100 mL) was added to 100 mg of the magnetized beads and was shaken at room temperature for 10 min. Thereafter, ammonium hydroxide (28%, 2 mL) was added to the bead dispersion and was shaken at room temperature for 20 min. To the dispersion TEOS (2 mL) was added and vigorously shaken at room temperature for 12 h. The resulting silica-coated magnetic beads were collected by magnet and washed five times with ethanol.

<Surface Modification of the Magnetic Beads>

The procedure described in the section <Surface modification of the multilayered multiple quantum dot-containing nanoparticles> of Example 1 was repeated.

<Antibody Conjugation>

An antibody (10 μM) was added to 100 μg of the surface modified magnetic beads, as shown in FIG. 7, and shaken at room temperature for 2 h. Thereafter, the mixture was washed four times with PBS (pH 7.2). A BSA solution (5% (w/w), 1 mL) was added to the antibody-conjugated magnetic beads, shaken at room temperature for 1 h, washed four times with PBS (pH 7.2), and dispersed in PBS (pH 7.2).

<Sandwich Immunoassay>

The antigen dispersed in PBS (pH 7.2) was added to 100 μg of the antibody-conjugated magnetic beads and shaken at room temperature for 1 h. Then, the mixture was washed four times with PBS (pH 7.2) using magnet, as shown on the right side of FIG. 7, and 100 μg of the antibody-bound multilayer quantum dot-containing nanoparticles were added thereto. The mixture was shaken at room temperature for 1 h, washed four times with PBS (pH 7.2) for 1 h, and dispersed in 300 μl of PBS (pH 7.2) to construct a bioplatform.

Quantitative fluorescence signals from the platform constructed in Application Example 2 were observed using a UV-vis spectrophotometer, as shown on the right side of FIG. 7. Specifically, 300 μl of the platform was filled in a black 96-well plate. The UV excitation wavelength was 385 nm and the emission wavelength was 625 nm.

FIG. 8 shows the application of the inventive multilayered multiple quantum dot-containing nanoparticles to a practical sandwich assay. As can be seen from the left side of FIG. 8, fluorescence was detected in more than the range of 3.2-$3.2 \times 10^{-4}$ HAU. As can be seen from the right side of FIG. 8, there was no significant difference when the same target material was detected by real-time PCR. These results concluded that the use of the inventive multilayered multiple quantum dot-containing nanoparticles enables accurate and fast diagnosis at a level comparable to that of real-time PCR and is effective in achieving a broad dynamic range of ≥log 10.

Each of the multilayered multiple quantum dot-doped nanoparticles according to the present invention has a structure consisting of a polymer or inorganic core particle, a quantum dot-embedded layer, and a silica/quantum dot composite shell. The multilayered multiple quantum dot-doped nanoparticles of the present invention can be used to detect biomolecules with improved quantum yield (QY) and brightness while maintaining a large area covered by the quantum dots and stable bonds of the quantum dots. Therefore, the multilayered multiple quantum dot-doped nanoparticles of the present invention are suitable for bioapplications, including bioplatforms and highly sensitive methods for detecting biomolecules.

The invention claimed is:

1. Quantum dot-doped nanoparticles, each of the quantum dot-doped nanoparticles comprises:
   a core particle, wherein the core particle is a polymer or inorganic material;
   a quantum dot-embedded layer, wherein the quantum dot-embedded layer consists of first multiple quantum dots bound to the outer surface of the core particle and the first multiple quantum dots surround the entire surface of the core particle;
   a silica/quantum dot composite shell, wherein the silica/quantum dot composite shell comprises second multiple quantum dots and a silica and surrounds the quantum dot-embedded layer;
   a first material comprising functional groups at opposite ends of the first material; and
   a second material comprising functional groups at opposite ends of the second material,
   wherein,
   the first material is present between the core particle and the first multiple quantum dots, and
   each of the first multiple quantum dots is bonded to one of the functional groups of the first material and the outer surface of the core particle is bonded to another of the functional groups of the first material such that each of the first multiple quantum dots is covalently bonded to the core particle.

2. The quantum dot-doped nanoparticles according to claim 1,
wherein each of the first multiple quantum dots of the quantum dot-embedded layer is linked with the silica of the silica/quantum dot composite shell such that the linking provides a structure in which the first multiple quantum dots are randomly bound to the silica.

3. The quantum dot-doped nanoparticles according to claim 2,
wherein the linking with the silica of the silica/quantum dot composite shell forms bonds by the second materials, wherein the functional group at one end of the second material is bound to the first multiple quantum dots and the functional group at the other end of the second material is bound to the silica.

4. The quantum dot-doped nanoparticles according to claim 1,
wherein the quantum dot-embedded layer is formed by multiple doping of quantum dots coated with a hydrophobic organic compound on the outer surface of the core particle and the doped quantum dots form layers sequentially surrounding the core particle.

5. The quantum dot-doped nanoparticles according to claim 1,
wherein the silica/quantum dot composite shell consists of a plurality of layers that are formed on the outer surface of the quantum dot-embedded layer to sequentially surround the quantum dot-embedded layer, wherein each of the plurality of layers consists of the second multiple quantum dots and the silica.

6. The quantum dot-doped nanoparticles according to claim 1,
further comprising a silica-based shell, wherein the silica-based shell surrounds the silica/quantum dot composite shell.

7. The quantum dot-doped nanoparticles according to claim 1,
wherein the quantum dots are of type I.

* * * * *